United States Patent [19]
Bodford et al.

[11] Patent Number: 5,643,239
[45] Date of Patent: Jul. 1, 1997

[54] BREATHABLE DISPOSABLE SANITARY PRODUCT CONSTRUCTION

[75] Inventors: Carl Allen Bodford, Charlottesville; Rahul Krishnakant Nayak, Stuarts Draft, both of Va.

[73] Assignee: Poly-Bond, Inc., Waynesboro, Va.

[21] Appl. No.: 552,727

[22] Filed: Nov. 3, 1995

[51] Int. Cl.$^6$ .............................. A61F 13/15; A61F 13/20
[52] U.S. Cl. .......................... 604/370; 604/366; 604/372; 604/378; 604/381
[58] Field of Search ................................ 604/358, 366, 604/370, 372, 378–382, 385.1, 385.2

[56] References Cited

U.S. PATENT DOCUMENTS

| | | | |
|---|---|---|---|
| 4,341,216 | 7/1982 | Obenour | 604/370 |
| 4,347,844 | 9/1982 | Ohki et al. | |
| 4,704,116 | 11/1987 | Enloe | |
| 4,725,473 | 2/1988 | Van Gompel et al. | |
| 4,818,600 | 4/1989 | Braun et al. | |
| 4,834,740 | 5/1989 | Suzuki et al. | |
| 5,019,062 | 5/1991 | Ryan et al. | |
| 5,114,418 | 5/1992 | Levy | |
| 5,190,533 | 3/1993 | Blackburn | |
| 5,257,982 | 11/1993 | Cohen et al. | |
| 5,263,948 | 11/1993 | Karami et al. | |
| 5,292,316 | 3/1994 | Suzuki | |
| 5,330,456 | 7/1994 | Robinson | |
| 5,342,334 | 8/1994 | Thompson et al. | 604/366 |
| 5,342,469 | 8/1994 | Bodford et al. | |
| 5,476,458 | 12/1995 | Glaug et al. | 604/378 |
| 5,492,751 | 2/1996 | Butt, Sr. et al. | |

Primary Examiner—John G. Weiss
Assistant Examiner—P. Zuttarelli
Attorney, Agent, or Firm—Amster, Rothstein & Ebenstein

[57] ABSTRACT

A breathable diaper, feminine hygiene, or like disposable sanitary product construction includes a plurality of materials comprising, from the skin-facing side outwardly a topsheet of liquid- and vapor-permeable hydrophilic material. A core of highly absorbent material disposed outwardly of the topsheet for absorbing fluid received through said topsheet. The core has an inner surface in fluid communication with the topsheet, an outer surface and two lateral side surfaces. A barrier is formed of a multilayer non-woven material which is hydrophobic and vapor-permeable for limiting the outward escape of fluid therethrough while enabling the outward escape of heat and water vapor therethrough, such as a two-layer spunbond-meltblown or a three-layer spunbond-meltblown-spunbond. In use, the barrier is in a U-shaped configuration having a base disposed adjacent the core outer surface and a pair of flanges upstanding from the base and each extending inwardly adjacent to a respective one of the core lateral side surfaces. A backsheet is formed of a multilayer non-woven material which is hydrophobic and vapor-permeable for limiting the outward escape of fluid therethrough while enabling the outward escape of heat and water vapor therethrough, such as a two-layer spunbond-meltblown or a three-layer spunbond-meltblown-spunbond. The backsheet is disposed at least partially outwardly of the barrier base.

24 Claims, 4 Drawing Sheets

BREATHABLE DISPOSABLE SANITARY PRODUCT CONSTRUCTION

BACKGROUND OF THE INVENTION

The present invention relates to breathable diapers, feminine hygiene or like disposable sanitary product constructions, and more particularly to such a construction which is breathable and has an outer or backsheet surface which is cloth-like.

Disposable diapers for infants and incontinent older people are a major industry and, as such, constitute a crowded art, competitively speaking. In general, such sanitary product constructions comprise, from the skin-facing side outwardly, an inner topsheet (also called a cover or front sheet) which is liquid-permeable to facilitate entry of the fluid exudate from the wearer into the construction, a core of highly absorbent material for absorbing fluid received through the topsheet, and an outer backsheet formed of a vapor- and liquid-impermeable plastic to eliminate leakage of fluid from the diaper.

Such diapers have not proven to be entirely satisfactory. While the inner topsheet is typically in the form of a cloth-like material having a soft hand (which is correctly perceived as being comfortable for the baby to have adjacent to its skin), the outer backsheet plastic presents a rather cold, clammy surface which is at least perceived of as inhospitable and uncomfortable for the baby's skin. Further, the feel of the plastic backsheet to the parent or caregiver is inhospitable and uncomfortable in comparison to conventional cloth diapers. While the outer backsheet is less likely to come into contact with the baby's skin then the inner topsheet, the plastic backsheet is still perceived of as a negative and presumably discourages potential customers for disposable diapers.

Further, the plastic backsheet is impervious not only to fluid, but generally to heat and water vapor as well. Accordingly, the moisture vapor and the heat generated by the bodily exudate trapped within the diaper lead to conditions adjacent the wearer's skin which promote skin irritation, infection, and the like.

While the plastic backsheet is generally effective in precluding the passage of bodily exudate outwardly therethrough where the highly absorbent core is present, it is not efficient in preventing side leakage—that is, lateral leakage of fluids from the opposed side portions of the core sidewards between the leg gathers of the backsheet and the baby's skin. The obvious solution to the problem—tightening of the leg gathers—in turn presented problems in terms of the comfort of the baby, skin irritation, etc.

Accordingly, it is an object of the present invention to provide in one preferred embodiment a breathable diaper, feminine hygiene or like disposable sanitary product construction which has a cloth-like outer backsheet surface.

Another object is to provide in one preferred embodiment such a construction which is breathable to enable the escape of water vapor and heat therethrough.

A further object is to provide in one preferred embodiment such a construction which efficiently limits side leakage.

It is also an object of the present invention to provide a preferred embodiment of a disposable sanitary product construction having a backsheet surface which is cloth-like and of good hand, is breathable, and affords an efficient system for limiting side leakage.

It is a further object to provide such a construction which is simple and inexpensive to manufacture.

SUMMARY OF THE INVENTION

It has now been found that the above and related objects of the present invention are obtained in a breathable diaper, feminine hygiene or like disposable sanitary product construction. The construction includes a plurality of materials comprising, from the skin-facing side outwardly, a topsheet, a core, a barrier and a backsheet. The topsheet is formed of liquid- and vapor-permeable hydrophilic material. The core is formed of highly absorbent material for absorbing fluid received through the topsheet. The core has an inner surface in fluid communication with the topsheet, an outer surface and two lateral side surfaces. The barrier is formed of a multilayer non-woven material which is hydrophobic and vapor permeable for limiting the outward escape of fluid therethrough while enabling the outward escape of heat and water vapor therethrough. In use the barrier is in a U-shaped configuration having a base disposed adjacent the core outer surface and a pair of flanges upstanding from the base, each flange extending inwardly adjacent to a respective one of the core lateral side surfaces. The backsheet is formed of a multilayer non-woven material which is hydrophobic and vapor permeable for limiting the outward escape of fluid therethrough while enabling the outward escape of heat and water vapor therethrough. The backsheet is disposed at least partially outwardly of the barrier base.

In a preferred embodiment, the backsheet and/or barrier material is SM, a two-layer spunbond-meltblown non-woven fabric formed of a spunbond layer and a meltblown layer. In an optimal embodiment, the backsheet and/or barrier material is SMS, a three-layer spunbond-meltblown-spunbond non-woven fabric formed of two spunbond layers and a meltblown layer disposed intermediate the spunbond layers and bonding them together. The construction may include an additive or coating which increases the hydrophobicity of the material.

The topsheet may be a one-layer spunbond non-woven material, a fluid-distributing material, or a two-layer fabric formed of an inner layer of a liquid and vapor-permeable hydrophilic non-woven material and an outer layer of a fluid-distributing material. Preferably the barrier base is thicker than the barrier flanges to further limit the outward escape of fluid therethrough, and a portion of the barrier flanges and backsheet material includes elastic material such that, in use, a portion of the barrier flanges and backsheet material are gathered about the legs of the user.

The construction preferably includes a hydrophobic enhancer formed of a multilayer non-woven material which is hydrophobic and vapor-permeable for limiting the outward escape of fluid therethrough while enabling the outward escape of heat and water vapor therethrough. The hydrophobic enhancer is disposed at least partially outwardly of the barrier base and inwardly of the backsheet. The hydrophobic enhancer is preferably SM or SMS. The hydrophobic enhancer may be a hydrophobic coating disposed adjacent an inner surface of the backsheet, the coating being polymeric, but cracked or fractured to provide breathability thereto. The cracked coating is preferably an ethyl vinyl acetate (EVA) extrusion having cracks or fractures sufficient to provide breathability thereto.

While in the embodiments described above the barrier flanges are contiguous to the core lateral side surfaces, the present invention also encompasses the variant wherein the topsheet defines a topsheet base disposed adjacent the core inner surface and a pair of topsheet flanges extending outwardly from the topsheet base. Each topsheet flange is secured to a respective barrier flange at a point spaced from the adjacent core lateral side surface.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
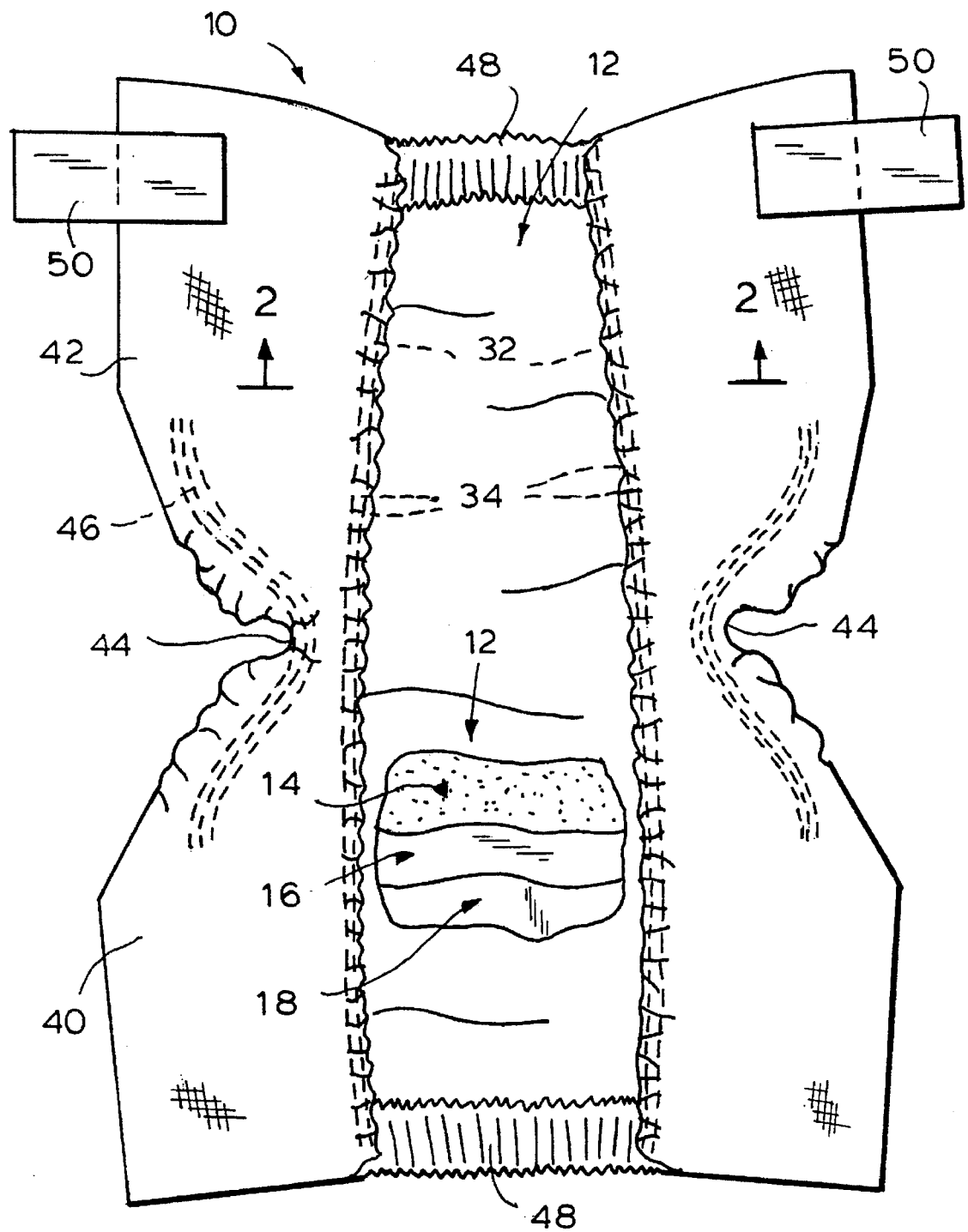
FIG. 1 is a top plan view of a simple embodiment of a diaper according to the present invention, with successive portions thereof being removed to reveal details of internal construction.
Figure 2:
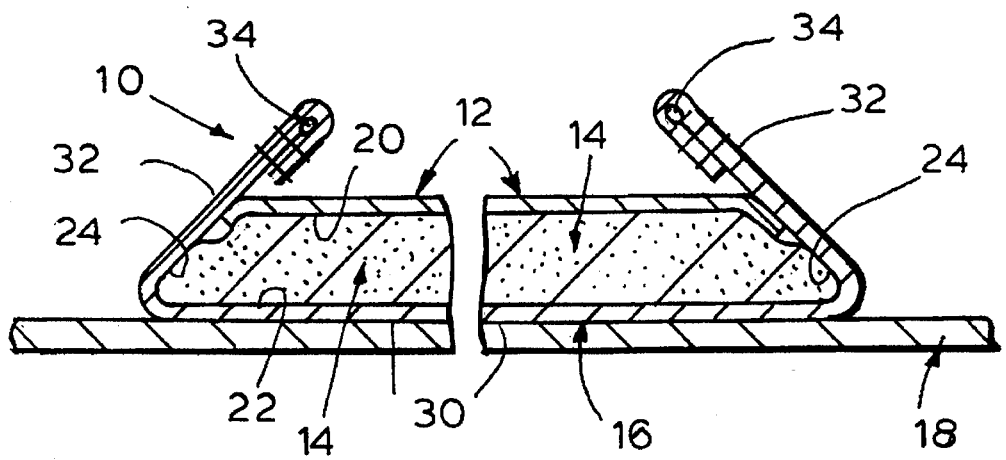
FIG. 2 is a sectional view thereof taken along the line 2—2 of FIG. 1.

Referring now to the drawing, and in particular to FIGS. 1 and 2 thereof, therein illustrated is a simple embodiment of a breathable diaper according to the present invention, generally designated by the reference numeral 10. As will be appreciated by those skilled in the art, the principles of the disposable sanitary product construction may be used for other disposable sanitary products such as feminine hygiene products, e.g., catamenial pads and the like, although typically the manner of securing the construction in place on the wearer's body will differ.

The construction 10 includes a plurality of materials comprising, from the skin-facing side outwardly, a topsheet generally designated 12, a core generally designated 14, a barrier generally designated 16, and a backsheet generally designated 18.

As is typical in these constructions, the topsheet 12 is formed of a liquid- and vapor-permeable hydrophilic material. For example, a preferred topsheet is formed of a one-layer, spunbond, non-woven fabric, with a soft, cloth-like surface for contact with the wearer's skin. While various liquid- and vapor-permeable hydrophilic materials may be used for the topsheet 12, a satisfactory diaper must be capable of providing the cloth-like inner surface affording good hand (e.g., softness).

Alternatively, the topsheet 12 may be formed of a fluid-distributing material, preferably one offering the same soft cloth-like feel as the spunbond topsheet. The fluid-distributing material performs a wicking service, drawing the fluid of the exudate away from the wearer and spreading it over a greater area of the topsheet 12 for transmission to the core 14.

Figure 4:
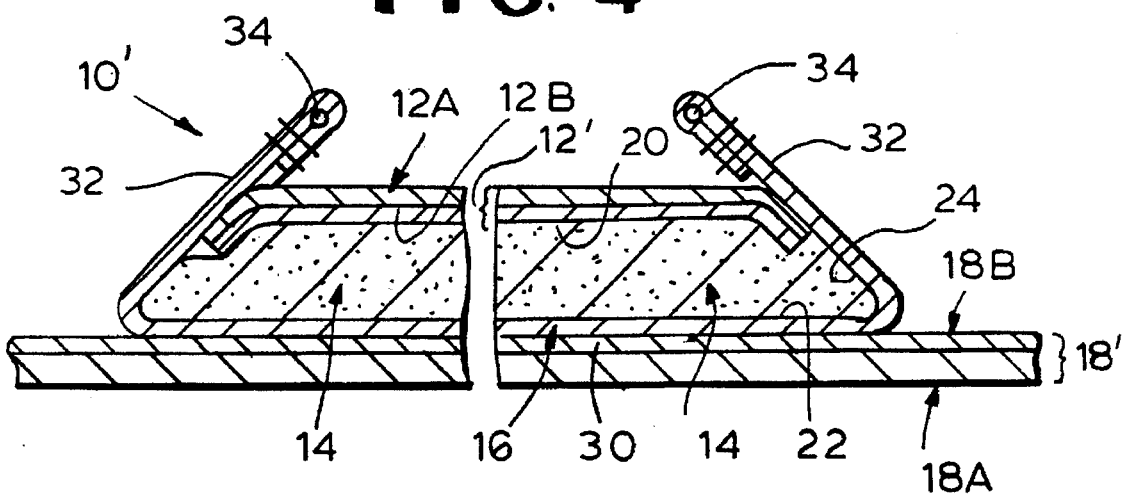
FIG. 4 is a sectional view thereof taken along the line 4—4 of FIG. 3.
Figure 3:
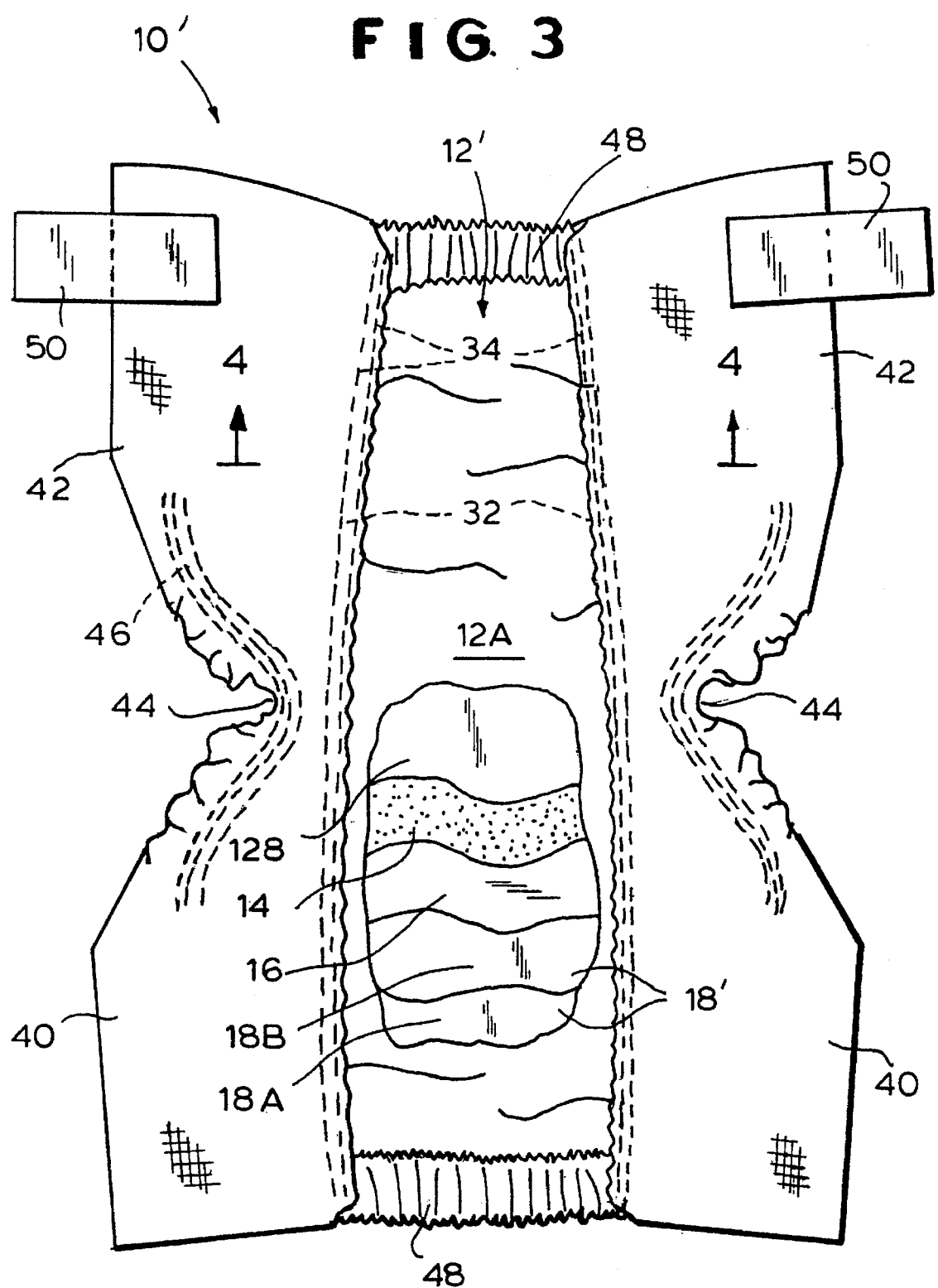
FIG. 3 is a top plan view of a more complex embodiment with successive portions thereof being removed to reveal details of internal construction.

In the preferred, more complex embodiment 10' of the diaper illustrated in FIGS. 3 and 4, the topsheet 12' is a two-layer fabric formed of an inner layer 12A of a liquid- and vapor-permeable, hydrophilic, non-woven material, and an outer layer 12B formed of a fluid-distributing material. Thus the preferred topsheet 12' is not only a liquid- and vapor-permeable hydrophilic material, but also a fluid-distributing material.

The topsheet 12 may comprise any of the materials heretofore employed for topsheets, e.g., spunbonded, polyester or polypropylene fibers, various non-woven fabrics, etc. having the desired wet and dry strengths as well as the liquid and vapor-permeablility and hydrophilic characteristics earlier mentioned.

Referring now to FIGS. 1–4, in both embodiments 10 and 10', the core 14 is formed of a highly absorbent material and is disposed outwardly of the topsheet 12, 12' for absorbing fluid received through the topsheet. The core 14 has an inner surface 20 in fluid communication with the topsheet, an outer surface 22, and two lateral side surfaces 24, 24. (Typically, the core 14 extends longitudinally along the crotch, with the lateral side surfaces thereof being generally parallel to that longitudinal axis.) The core may be composed of any of the absorbent materials heretofore employed for that purpose in the diaper art, e.g., wood pulp or fluff, absorbent cotton fibers, polyester or polypropylene and the like, including mixtures thereof. Preferably, the core 14 is formed of a superslurper or like material which wicks the fluid received from the topsheet through and away from the topsheet, so that the topsheet generally presents a relatively dry inner surface to the wearer. As highly absorbent materials suitable for the core are well known in the conventional diaper, feminine hygiene and like sanitary product constructions art, further details thereof need not be provided herein.

The barrier 16 is disposed partially outwardly of the core 14 and is formed of a multilayer, non-woven material which is hydrophobic and vapor-permeable for limiting the outward escape of fluid therethrough, while enabling the outward escape of heat and water vapor therethrough. It has been found that the heat and humidity released by the accumulated body exudates, such as urine and feces, promote the irritation and itching which frequently develops when conventional disposable diapers are used. The barrier 16 of the present invention enables the heat and water vapor to escape outwardly from the core 14, through the barrier 16 and then further outwardly while at the same time limiting the outward escape of fluid (e.g., urine, blood, etc.) therethrough. The non-woven material may be spunbond, carded, spun-laced, meltblown or the like. A chemical finish may be applied in order to enhance its ability to repel specific fluids. The preferred materials are polyethylene, polypropylene, and the like.

Figure 5:
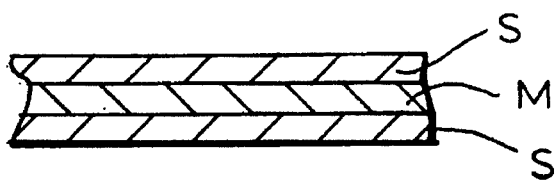
FIG. 5 is a fragmentary sectional view of a multilayered non-woven material—namely, a spunbond-meltblown-spunbond material.

The barrier material 16 is preferably SM or optimally SMS. SM is a two-layer spunbond-meltblown non-woven fabric formed of a spunbond layer and a meltblown layer. When SM is used, the meltblown layer is typically the inner layer. Referring now to FIG. 5, SMS is a three-layer, spunbond-meltblown-spunbond non-woven fabric formed of two spunbond layers S and a meltblown layer M disposed intermediate the spunbond layers and bonding them together. The spunbond and meltblown layers are typically formed of the same composition—preferably either polyethylene or propylene—although different compositions formed of other natural or synthetic materials may be used. Typically, the meltblown material is similar to the spunbond material, except that the fiber lengths are substantially smaller (such that the meltblown material by itself lacks tenacity and cannot used by itself). Multilayer non-woven materials which are hydrophobic and vapor-permeable (i.e., water vapor-permeable) are well known in the art, and accordingly it is not deemed necessary to set forth herein further details thereof. It will be appreciated, however, that the layers forming the SM or SMS material may contain conventional additives to increase the hydrophobicity of the material, or even a coating, so long as the aforementioned desirable properties of the material are that adversely affected.

When the diaper is in use, as illustrated in FIG. 2, barrier 16 is U-shaped in cross-section and has a base 30 at least partially disposed adjacent the outer surface 22 of the core 14 and a pair of flanges 32 upstanding from the base 30. Each of the flanges 22 extends inwardly (towards the topsheet 12) closely adjacent to a respective one of the core lateral side surfaces 24.

Even after distribution over the major face of the core 14 by a fluid-distributing topsheet 12, 12', the fluid passing from the core 14 to the barrier 16 still tends to bunch at the center of the core 14 rather than at the lateral sides 24 thereof. Accordingly, preferably the barrier base 30 is thicker than the barrier flanges 32, thereby to further limit the outward escape of fluid through the barrier base 30.

A portion of the barrier flanges 32, especially adjacent the free ends thereof, includes elastic or other biasing material 34 such that, when worn, a portion of the barrier flanges 32 are gathered about the legs of the user, thereby to prevent the escape of fluid laterally from the diaper. The elastic material 34 may be embedded in a folded-over free end of the barrier flanges 32, as illustrated, or it may simply be glued or stitched thereto. Thus, when the diaper 10 or 10' is tautly stretched out, as illustrated in FIGS. 1 and 3, the barrier flanges 32 lay flat over the topsheet 12 or 12' and core 14 while, when the diaper is worn as illustrated in FIGS. 2 and 4, the barrier flanges 32 stand upright to prevent the lateral escape of fluid exudate from the diaper. Optionally the free ends of the barrier flanges 32 may be secured to the lateral edges of the top sheet 12 to limit fluid leakage therebetween.

It will be appreciated that the core 14 is encapsulated on all four sides: by the topsheet 12, 12' on its inner surface 20, the barrier base 30 on its outer surface 22, and the barrier flanges 32 on its lateral sides 24.

The backsheet 18, like the barrier 14, is formed of a multilayer non-woven material which is hydrophobic and vapor-permeable for limiting the outward escape of fluid therethrough while enabling the escape of heat and water-vapor therethrough. The preferred backsheet material is a two-layer SM or a three-layer SMS, as described supra. The backsheet 18 is at least partially disposed outwardly of the barrier base 30. Any fluid which passes out of the core 14 and through the barrier 16 encounters the backsheet 18, which further limits its outward escape.

The backsheet 18 is typically formed in the configuration of a conventional diaper having a front portion 40, a rear portion 42 and a crotch portion 44 therebetween. The crotch portion 44 typically includes elastic threads 46 for gathering the backsheet 18 around the legs of the wearer. The central longitudinal portion of the backsheet 18 may define gathers 48 at its opposed waist ends to assist in shaping the diaper and keeping the various components thereof in place—for example, by stitching therethrough to drape the gathers 48.

Conventional tape fasteners 50, such as adhesive or VELCRO tabs, are permanently fastened to the rear portion 42 of backsheet 18 so that they may be releasably attached to the front portion 40 when the diaper is placed on the wearer. The pair of conventional fasteners in the waist area permit releasably securing or refastening of the opposed ends of the backsheet 18 together around the waist of the wearer where the diaper is folded to engage the front and back of the body. The fasteners may employ refastenable pressure-sensitive adhesive and may be elastic in nature.

The presence of a backsheet 18 formed of a multilayer, non-woven material enables the outer surface of the diaper to have an outer surface with a cloth-like feel similar to that of a conventional cloth diaper. Accordingly, a potential purchaser of the diaper will be under the impression that he/she is affording twice the comfort and protection of a conventional diaper because a soft, cloth-like material forms both the topsheet 12 and the backsheet 18.

In the preferred, albeit more complex, embodiment 10' of the present invention illustrated in FIGS. 3 and 4, the construction 10' includes the backsheet 18' defining diaper outer surface 18A and a hydrophobic enhancer 18B formed of a multilayer, non-woven material. The multilayer, non-woven material of enhancer 18B is hydrophobic and vapor-permeable for limiting the outward escape of fluid therethrough while enabling the outward escape of heat and water vapor therethrough. The preferred enhancer material is a two-layer SM or a three-layer SMS as described, supra.

Preferably the hydrophobic enhancer 18B is at least partially disposed outwardly of the barrier base 30 and inwardly of the backsheet 18A. Indeed, the hydrophobic enhancer 18B may simply be a coating disposed adjacent the inner surface of backsheet 18A. The hydrophobic coating is preferably cracked or fractured to provide breathability thereto. Preferred coatings are polymers—e.g., an ethyl vinyl acetate (EVA) extrusion having cracks or fractures sufficient to provide breathability therethrough. It will be appreciated that the presence of the enhancer 18B as either a separate layer or as a coating on the inner surface of backsheet 18A does not detract from the desirable soft feel of the latter.

Fluid exudate escaping from the lateral sides of the core 14 are initially blocked by the barrier 16 and trapped in the U-shaped well 32, 30, 32 of the barrier 16. Even if the fluid exudate escapes the well of the barrier, it is still retained within the diaper by the backsheet 18 or the hydrophobic enhancer 18B and backsheet 18A, depending upon the embodiment of the diaper.

The various materials 12, 14, 16, 18 of diaper 10 or 12A, 12B, 14, 16, 18A, 18B of diaper 10' may be secured together with hot-melt or like adhesives or even simple mechanical or stitching means, as is customary in the diaper art.

The diaper 10, 10' according to the present invention is used in the same manner as a conventional diaper.

Figure 6:
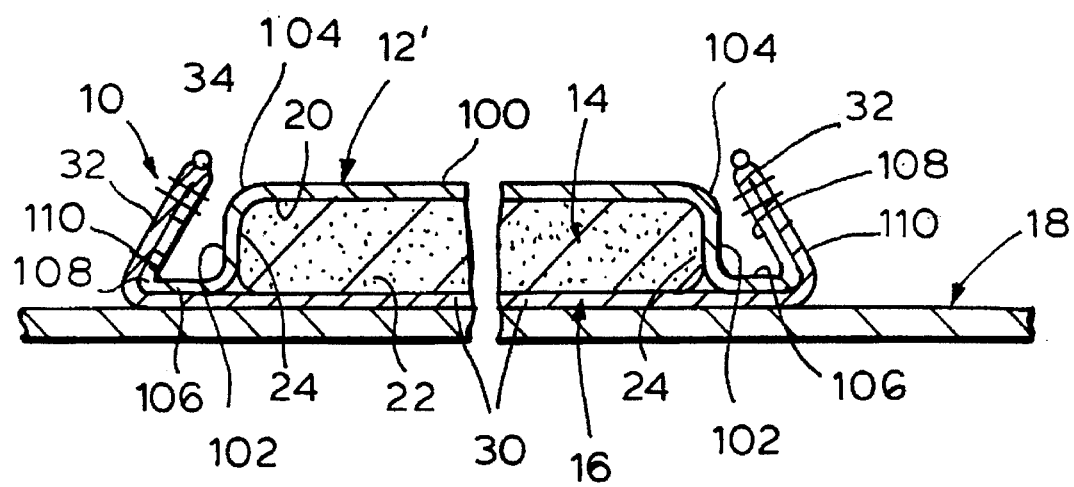
FIG. 6 is a sectional view of a variant of the simple embodiment.
Figure 7:
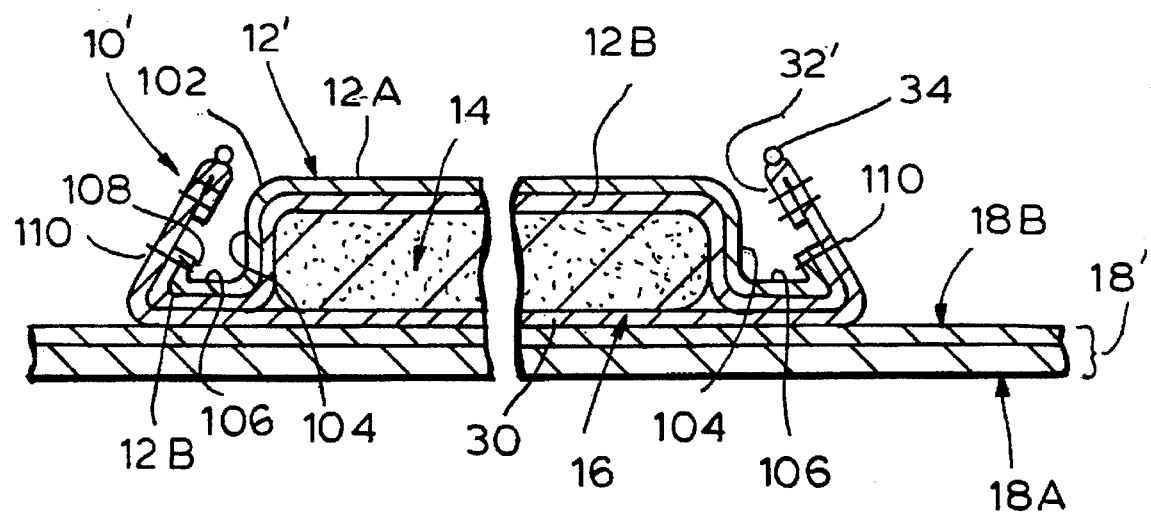
FIG. 7 is a sectional view of a variant of the complex embodiment.

While the embodiments illustrated in FIGS. 1–4 have the barrier flanges 32 disposed contiguous to the core lateral side surfaces 24, and only optionally secured to the topsheet 12, alternatively the topsheet 12 and the barrier 16 may be directly secured together at a location optionally spaced from core 14. Thus, as illustrated in FIG. 6, the topsheet 12' defines a topsheet base 100 disposed adjacent the core inner surface 20 and a pair of topsheet flanges 102 extending outwardly from the topsheet base 100. The topsheet flanges 102 are U-shaped, each topsheet flange 102 having one leg 104 disposed contiguous to or very closely adjacent to the core lateral side surface 24, the topsheet base 106 being disposed generally parallel to the barrier base 30, and the other topsheet flange leg 108 being secured to the barrier flange 32, as illustrated at 110. As illustrated in FIG. 7, clearly the principles of this variant are equally applicable to a variant of the more complex embodiment illustrated in FIGS. 3 and 4, and, indeed, the configuration of the topsheet flanges and the barrier flanges may be varied substantially as long as each topsheet flange is secured to a respective barrier flange in such a manner as to minimize side leakage.

To summarize, the present invention provides a breathable diaper, feminine hygiene or like disposable sanitary product construction which has a cloth-like outerback sheet surface, is breathable to enable the escape of water vapor and heat therethrough, and efficiently limits side leakage of fluid. The construction is simple and inexpensive to manufacture.

Now that the preferred embodiments of the present invention have been shown and described in detail, various modifications and improvements thereon will become readily apparent to those skilled in the art. Accordingly, the spirit and scope of the present invention is to be interpreted broadly and limited only by the appended claims, and not by the foregoing specification.

We claim:

1. A breathable diaper, feminine hygiene, or like disposable sanitary product construction including a plurality of materials comprising, from the skin-facing side outwardly:

(A) a topsheet of liquid- and vapor-permeable hydrophilic material;

(B) a core of highly absorbent material disposed outwardly of said topsheet for absorbing fluid received through said topsheet, said core having an inner surface in fluid communication with said topsheet and an outer surface;

(C) a barrier formed of a multilayer non-woven material which is hydrophobic and vapor-permeable for limiting the outward escape of fluid therethrough while enabling the outward escape of heat and water vapor therethrough, said barrier having a base disposed adjacent said core outer surface; and (D) a backsheet formed of a multilayer non-woven material which is hydrophobic and vapor permeable for limiting the outward escape of fluid therethrough while enabling the outward escape of heat and water vapor therethrough, said backsheet being disposed at least partially outwardly of said barrier base.

2. The construction of claim 1 wherein said backsheet material is a two-layer spunbond-meltblown non-woven fabric formed of a spunbond layer and a meltblown layer.

3. The construction of claim 1 wherein said backsheet material is a three-layer spunbond-meltblown-spunbond non-woven fabric formed of two spunbond layers and a meltblown layer disposed intermediate said spunbond layers and bonding them together.

4. The construction of claim 1 including an additive or coating which increases the hydrophobicity of said backsheet material.

5. The construction of claim 1 wherein a portion of said backsheet material includes elastic material such that, in use, a portion of said backsheet material is gathered about the legs of the user.

6. The construction of claim 1 wherein said barrier material is a two-layer spunbond-meltblown non-woven fabric formed of a spunbond layer and a meltblown layer.

7. The construction of claim 1 wherein said barrier material is a three-layer spunbond-meltblown-spunbond non-woven fabric formed of two spunbond layers and a meltblown layer disposed intermediate said spunbond layer and bonding them together.

8. The construction of claim 1 including an additive or coating which increases the hydrophobicity of said barrier material.

9. The construction of claim 1 wherein said topsheet is a one-layer spunbond non-woven material.

10. The construction of claim 1 wherein said topsheet is formed of a fluid-distributing material.

11. The construction of claim 1 wherein said topsheet is a two-layer fabric formed of an inner layer of a liquid and vapor permeable hydrophilic non-woven material and an outer layer of a fluid-distributing material.

12. The construction of claim 1 which includes a hydrophobic enhancer formed of a multilayer non-woven material which is hydrophobic and vapor-permeable for limiting the outward escape of fluid therethrough while enabling the outward escape of heat and water vapor therethrough, said hydrophobic enhancer being disposed at least partially outwardly of said barrier base and inwardly of said backsheet.

13. The construction of claim 12 in which said hydrophobic enhancer is a two-layer spunbond-meltblown non-woven fabric formed of a spunbond layer and a meltblown layer.

14. The construction of claim 12 in which said hydrophobic enhancer is a three-layer spunbond-meltblown-spunbond non-woven fabric formed of two spunbond layers and a meltblown layer disposed intermediate said spunbond layer and bonding them together.

15. The construction of claim 1 including a hydrophobic coating disposed adjacent an inner surface of said backsheet.

16. The construction of claim 15 wherein said coating is cracked or fractured to provide breathability thereto.

17. The construction of claim 16 wherein said cracked coating is polymeric.

18. The construction of claim 16 wherein said cracked coating is an ethyl vinyl acetate (EVA) extrusion having cracks or fractures sufficient to provide breathability thereto.

19. The construction of claim 1 wherein said core also has two lateral side surfaces and in use said barrier has a U-shaped configuration with a pair of flanges upstanding from said barrier base, each said flange extending inwardly adjacent to a respective one of said core lateral side surfaces.

20. The construction of claim 19 wherein said barrier base is thicker than said barrier flanges to further limit the outward escape of fluid therethrough.

21. The construction of claim 19 wherein a portion of said barrier flanges includes elastic material such that in use a portion of said barrier flanges are gathered about the legs of the user.

22. The construction of claim 19 wherein said barrier flanges are contiguous to said core lateral side surfaces.

23. The construction of claim 19 wherein said topsheet defines a topsheet base disposed adjacent said core inner surface and a pair of topsheet flanges extending from said topsheet base, each topsheet flange being secured to a respective barrier flange.

24. A breathable diaper, feminine hygiene, or like disposable sanitary product construction including a plurality of materials comprising, from the skin-facing side outwardly:

(A) a vapor-permeable topsheet of hydrophilic, fluid-distributing, non-woven material, said topsheet including an inner layer of hydrophilic non-woven material and an outer layer of fluid-distributing material;

(B) a core of highly absorbent material disposed outwardly of said topsheet for absorbing fluid received through said topsheet, said core having an inner surface in fluid communication with said topsheet, an outer surface and two lateral side surfaces;

(C) a hydrophobic and vapor-permeable barrier formed of a three-layer spunbond-meltblown-spunbond non-woven fabric formed of two spunbond layers and a meltblown layer disposed intermediate said spunbond layers and bonding them together, for limiting the outward escape of fluid therethrough while enabling the outward escape of heat and water vapor therethrough, in use said barrier being in a U-shaped configuration having a base disposed adjacent said core outer surface and a pair of flanges upstanding from said base and each extending inwardly adjacent to a respective one of said core lateral side surfaces;

(D) a vapor-permeable hydrophobic enhancer formed of a three-layer spunbond-meltblown-spunbond non-woven fabric formed of two spunbond layers and a meltblown layer disposed intermediate said spunbond layers and bonding them together, for limiting the outward escape of fluid therethrough while enabling the outward escape of heat and water vapor therethrough, said enhancer being disposed at least partially outwardly of said barrier; and (E) a hydrophobic and vapor-permeable backsheet formed of a three-layer spunbond-meltblown-spunbond non-woven fabric formed of two spunbond layers and a meltblown layer disposed intermediate said spunbond layers and bonding them together, for limiting the outward escape of fluid therethrough while enabling the outward escape of heat and water vapor therethrough, said backsheet being disposed at least partially outwardly of said enhancer.

* * * * *